United States Patent [19]
Dial

[11] Patent Number: 5,824,024
[45] Date of Patent: *Oct. 20, 1998

[54] ILLUMINATION DEVICES AND METHODS FOR TREATING LIGHT DEFICIENCY AND MOOD DISORDERS

[76] Inventor: Daniel Christoper Dial, SE. 141 Mill Creek Rd., Shelton, Wash. 98584

[*] Notice: This patent issued on a continued prosecution application filed under 37 CFR 1.53(d), and is subject to the twenty year patent term provisions of 35 U.S.C. 154(a)(2).

[21] Appl. No.: 642,580

[22] Filed: May 3, 1996

[51] Int. Cl.⁶ ........................................ A61N 5/06
[52] U.S. Cl. ................................ 607/88; 600/27
[58] Field of Search ................ 607/88–89, 90, 607/93; 600/21, 27; 601/15

[56] References Cited

U.S. PATENT DOCUMENTS

| | | | |
|---|---|---|---|
| 5,046,494 | 9/1991 | Searfoss et al. | 600/27 X |
| 5,047,006 | 9/1991 | Brandston et al. | 600/27 X |

OTHER PUBLICATIONS

A. J. Lewy, Treating Chronobiologic Sleep and Mood Disorders with Bright Light, *Psychiatric Annals* 17:10, pp. 664–669, 10 Oct. 1987.

The SunBox® Co., Sun Light Jr. Advertisement, *The SunBox®Co.*, Jul. 1995.

The SunBox® Co., SunRizr™ Dawn/Dusk Simulator and Bio–Brite Light Visor™, *The SunBox®Co.*, Jul. 1995.

*Primary Examiner*—Jeffrey R. Jastrzab
*Assistant Examiner*—Ryan Carter
*Attorney, Agent, or Firm*—Ann W. Speckman

[57] ABSTRACT

Illumination fixtures for use in treating light deficiency and mood disorders, as well as color therapy, are disclosed. The fixtures employ an illumination gas having a high neon gas content. Fixtures in which the glass tubing is bent and convoluted in a three dimensional arrangement provide a high level of illumination in a compact device and substantially reduce glare. Fixtures employing multiple color tubing, dimmer(s) and/or timer(s) may be used to simulate natural lighting conditions, such as sunrise, neon illumination sources may also be used in combination with an as a source for fiber optic cables.

13 Claims, 5 Drawing Sheets

ILLUMINATION DEVICES AND METHODS FOR TREATING LIGHT DEFICIENCY AND MOOD DISORDERS

FIELD OF THE INVENTION

The present invention relates to illumination devices for use in treating conditions by exposure to a light source, such as light deficiency and mood disorders, as well as for color therapy and other types of light therapy. The illumination source of the present invention is especially useful for treating seasonal affective disorder. The invention furthermore relates to improved methods for treating various conditions using specified illumination sources.

BACKGROUND OF THE INVENTION

The psychological and physical effects of light deficiency and mood disorders are well established. Various forms of light therapy may be useful treatment for depression, sexual dysfunction, visual disorders, pre-menstrual syndrome ("PMS"), stress, learning disabilities and immune system deficiencies.

Winter depression, or seasonal affective disorder ("SAD"), for example, may affect up to 20% of the population in certain geographical areas and is associated with reduced exposure to natural light during the winter season. The most common symptoms are depression, fatigue, withdrawal and changes in appetite and sleep patterns. Light therapy, in which patients are exposed to bright light, is the conventional treatment and has proved to be an effective treatment for many SAD sufferers. In light therapy, artificial light is used to simulate sunlight, which is generally from about 10 to about 200 times as bright as "normal" indoor light.

Light sources used for treating light deficiency disorders such as SAD typically employ bright incandescent, fluorescent or halogen light bulbs. One commonly used device is a light box comprising an array of fluorescent bulbs with a diffusing screen mounted behind the tubes. The patient is exposed to the light by positioning himself or herself in proximity to the light box for a period of time ranging from about thirty minutes to several hours, depending on the level of illumination, light source, distance from illumination source, individual response, and the like. Treatments are generally administered on a frequent, often daily, basis. Research has suggested that the level of illumination is a critical aspect of the treatment. Some studies have suggested that the optimal level of illumination is one that matches the level of "natural" light shortly after sunrise or before sunset.

Conventional light boxes employing fluorescent tube illumination sources have several disadvantages. To achieve a sufficiently bright level of illumination, numerous fluorescent bulbs are required, and the light boxes consequently consume a significant amount of space and have a large footprint. They are unattractive and unwieldy. Additionally, fluorescent light sources tend to flicker, causing variations in illumination output that can produce irritability, headache, eye strain and, in severe cases, may cause migraine headaches. Fluorescent tubes also produce glare, which can induce unpleasant side effects such as headaches and eye strain.

Illumination devices that simulate sunrise or sunset, or some other natural lighting condition, are also used to treat patients having sleep disorders such as advanced or delayed sleep syndrome. Similarly, controlled exposure to bright light has been demonstrated to be effective for treating other types of problems such as jet lag, circadian rhythm abnormalities, and the like. Light sources used for treating sleep disorders are generally similar to the light boxes described above and suffer from similar disadvantages.

Illumination devices are also used in the practice of color therapy, which involves exposing patients to illumination of a selected wavelength band. Preferential exposure to selected wavelength light is believed to stimulate both metabolic and psychological responses. Illumination devices for use in color therapy generally employ incandescent, fluorescent or halogen light sources with filters to select for the appropriate wavelength band.

SUMMARY OF THE INVENTION

The illumination source of the present invention employs a neon-containing illumination gas. Fixtures generally referred to as "neon" frequently contain argon as an illumination gas-in combination with mercury vapor because argon is a less expensive gas than neon and has similar illumination properties. Preferred illumination sources of the present invention utilize an illumination gas comprising at least about 50% neon gas with mercury vapor. Combinations of neon with other suitable illumination gases may be used, provided that neon is a substantial constituent. Neon-containing illumination sources may produce bright illumination suitable for treatment of light deficiency and mood disorders, as well as saturated light of a selected wavelength for color therapy. The conditions referred to in this application collectively as "light deficiency and mood disorders" include depression, SAD, stress, learning disabilities, PMS, sexual dysfunctions, visual disorders, immune and nervous system abnormalities, sleep and other natural rhythm disorders, and other similar types of conditions.

Neon illumination sources of the present invention may be manufactured according to conventional techniques. Neon fixtures generally comprise a vacuum-sealed glass tube containing an illumination gas with an electrode at each end. The electrodes are electrically connected to an electrical transformer that, when activated, causes the illumination gas to glow. The color of the fixture depends on the phosphor coating on the inside surface of the glass tube. The fixture according to the present invention preferably comprises tubing having multiple bends and convolutions to provide a high level of illumination in a compact device having a relatively small footprint. The bent and convoluted tubing furthermore provides an illumination source in which glare and the consequent side effects are substantially eliminated.

Numerous advantages are realized by using a neon-containing gas as an illumination source. Neon-containing fixtures do not produce as much heat as many other illumination sources and, consequently, can be operated for longer time periods and require less cooling. The use of a neon-containing illumination gas substantially eliminates the flicker and illumination variances associated with fluorescent light fixtures and argon-containing fixtures, and reduces the incidence of side effects such as headache, irritability, eye strain, and the like. Neon-containing fixtures have a long life span and, if manufactured properly, generally do not require replacement.

White light produced by suitable phosphor coatings is generally preferred for treating light deficiency and mood disorders because it provides a suitably high level of illumination. Neon fixtures having tubing with different phosphor coatings producing light in selected wavelength bands have a high color saturation which is especially suitable for color therapy. Illumination sources emitting a single color may be provided for specialized color therapy treatments, or color tubing may be combined with white or other colors.

Numerous accessory features may be provided in connection with the neon illumination source. For example, a dimmer that permits the user to adjust the level of illumination emitted by the fixture is an optional feature. The exposure time for treatment of light deficiency and mood disorders is generally related to the illumination level, and the treatment time may therefore be varied by adjusting the illumination level. Timers may also be provided. A fixture employing multiple color tubes, dimmer(s) and timer(s) may be employed, for example, to simulate lighting conditions such as sunrise, sunset or the like.

Neon illumination sources may also be used in combination with and as a source for fiber optic cables. Light of a selected wavelength, for example, may be provided through fiber optic cable(s) as a focused source that may be directed to points, such as acupressure or acupuncture points, for various treatments. Fiber optic cable(s) may be terminated in a wand-type structure for this application. Alternatively, fiber optic cable(s) may be used in connection with accessories, such as modified eyeglasses, that direct light into the eyes. Illumination sources using fiber optic cables may provide more effective and efficient treatment by providing a more focused source, while providing the appropriate level of illumination and/or color saturation. Combinations of one or more neon-containing fixtures with fiber optic cables may be used in a variety of ways to deliver light for therapeutic purposes.

BRIEF DESCRIPTION OF THE FIGURES

The invention will be described below in detail with reference to the following figures, in which.

DESCRIPTION OF PREFERRED EMBODIMENTS

Figure 1A:
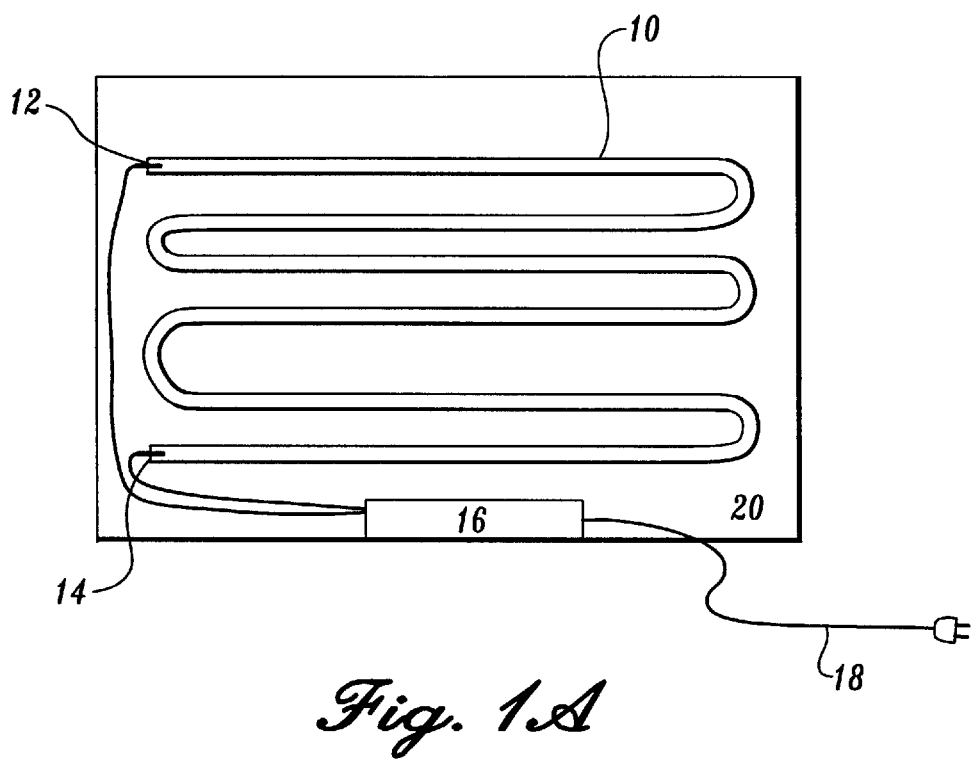
FIGS. 1A and 1B schematically illustrate neon fixtures according to the present invention arranged in generally two dimensional arrays, with FIG. 1A illustrating a generally "linear" arrangement and FIG. 1B illustrating a "convoluted" arrangement.

Commercial grade "neon" light fixtures generally utilize a gas mixture comprising about 35% neon and 65% argon with mercury vapor. The term "neon fixture" or "illumination gas," as used in this specification, means a fixture or illumination gas mixture comprising at least about 50% neon gas in addition to mercury vapor. Neon fixtures according to the present invention preferably comprise in excess of about 80% neon gas, and especially preferred embodiments employ essentially pure neon gas with mercury vapor.

Suitable tubing generally ranges from about 7 mm to about 18 mm in diameter. Smaller diameter tubing generally produces the brightest light, and is thus preferred for applications requiring bright light. Larger diameter tubing generally produces softer light that may be suitable for color therapy and other applications that don't require bright light.

Standard glass tubing and manufacturing techniques may be used to produce the neon fixtures of the present invention. The glass tubing containing the illumination gas may be provided in various configurations, depending upon the intended use. A suitable fixture may be arranged as a generally two dimensional array, or tubing may be bent and convoluted to provide a three dimensional arrangement in which relatively large illumination surface area, and consequently a relatively high level of illumination, is provided in a relatively small volumetric space. Additionally, highly convoluted tubing provides a fixture in which the axis is continuously variable and scatters light randomly, reducing glare and associated side effects. According to a preferred embodiment, an individual length of glass tubing is bent and convoluted, then fused to another length of tubing, which is then bent and convoluted, and the process is repeated until the desired length of tubing has been incorporated. Double compound bends produce the desired degree of compactness. Glass tubing having different types of phosphor coatings producing different colors of light may also be incorporated in a single fixture.

After the glass tubing is configured as desired, an electrode is welded to each end of the tubing using conventional manufacturing techniques. The glass tubing is then affixed to a bombarding table and conventional techniques are employed to verify hermeticity, bombard, inject illumination gas, and vacuum seal the tubing. The gas density, or pressure, depends on the diameter of the tubing. For example, glass tubing having a diameter of about 7 mm generally confines an illumination gas mixture at about 15 mm Hg pressure, while glass tubing having a diameter of about 18 mm confines an illumination gas at about 7 mm pressure. The desired gas pressure will depend upon the gas mixture, enclosure size and length, and the like, and may be determined by one of ordinary skill in the art.

Sufficient gas volume and illumination surface area are provided to produce the desired illumination output. The preferred illumination output capacity for neon fixtures for use in treating light deficiency and mood disorders may be specified by a health care professional. The illumination recommended for treating SAD, for example, is at least about 2500 lux. The composition of the gas mixture, diameter length and configuration of the tubing, and distance from the illumination source influence the illumination output. In general, neon fixtures producing white light and having an output of from about 2,500 to about 10,000 lux at a distance of about 18 inches or more from the illumination source are preferred for treatment of SAD and other light deficiency and mood disorders. Fixtures for treating light deficiency and mood disorders preferably employ glass tubing having a diameter of at least about 10 mm and a length of at least about 12 feet. The bulk of the bent and convoluted tubing preferably consumes a volume equal to or less than about 1.5 cubic foot. This embodiment provides a compact device capable of providing the desired illumination output and radiates light in all directions, thereby substantially eliminating glare. Moreover, because light is radiated in all directions, the fixture may be used by several people simultaneously.

Glass tubing having a phosphor coating that produces white light is preferred for treatment of light deficiency and mood disorders. Glass tubing having phosphor coatings that produce color in a specified, relatively narrow wavelength bandwidth is preferred for use in fixtures for color therapy. Especially suitable wavelengths for use in color therapy include wavelengths ranging from about 4700–5000 angstroms (in the blue range); from about 5000–5500 angstroms (in the green range); from about 6000–6700 angstroms (in the red range), as well as pink, yellow, purple, violet, orange, and other shades and combinations of shades.

Figure 1B:
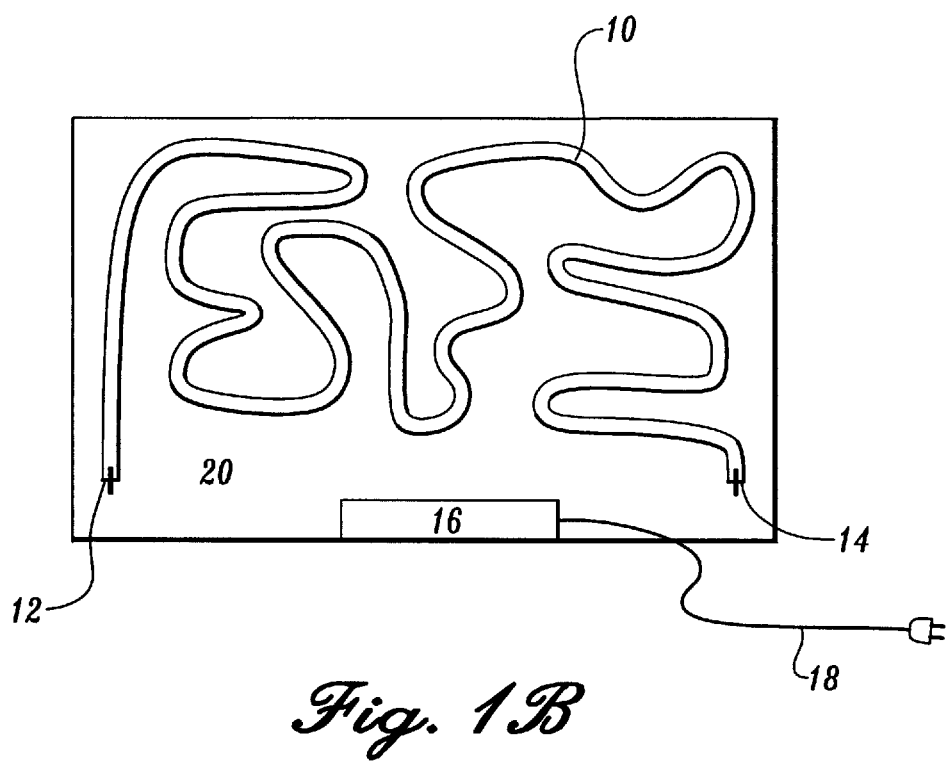

The figures illustrate preferred embodiments of neon fixtures according to the present invention. FIG. 1A shows a neon fixture having glass tubing 10 arranged in a generally two-dimensional, linear array. Tubing 10 may be mounted to any type of rigid support structure housing the fixture. Electrodes 12, 14 are hermetically sealed to the ends of glass tubing 10 and are electrically connected to transformer 16. Transformer 16 is electrically connectable to an external source of power such as an electrical outlet, by means of power cord 18. Reflective surface 20 is provided in proximity to glass tubing 10 to effectively increase the illumination output of the fixture. The reflective surface may be planar, as illustrated, or it may have multi-planar, hinged surfaces to direct the illumination toward a particular target. Numerous light reflective surfaces, such as white plexiglass, would be suitable. FIG. 1B illustrates a neon fixture having the same general arrangement, except that glass tubing 10 is provided as a generally two-dimensional, non-linear convoluted array.

The length or surface area of tubing 10 used in a fixture of the type illustrated in FIGS. 1A or 1B depends on the light requirements for particular applications. The tubing length and diameter may be adjusted, for example, to provide the desired illumination (lux) output for treating light deficiency and mood disorders. Similarly, one or more colors may be provided for color therapy applications. Treatment using these devices involves positioning a patient facing the fixture and exposing the patient to light for the prescribed length of time.

Figure 2:
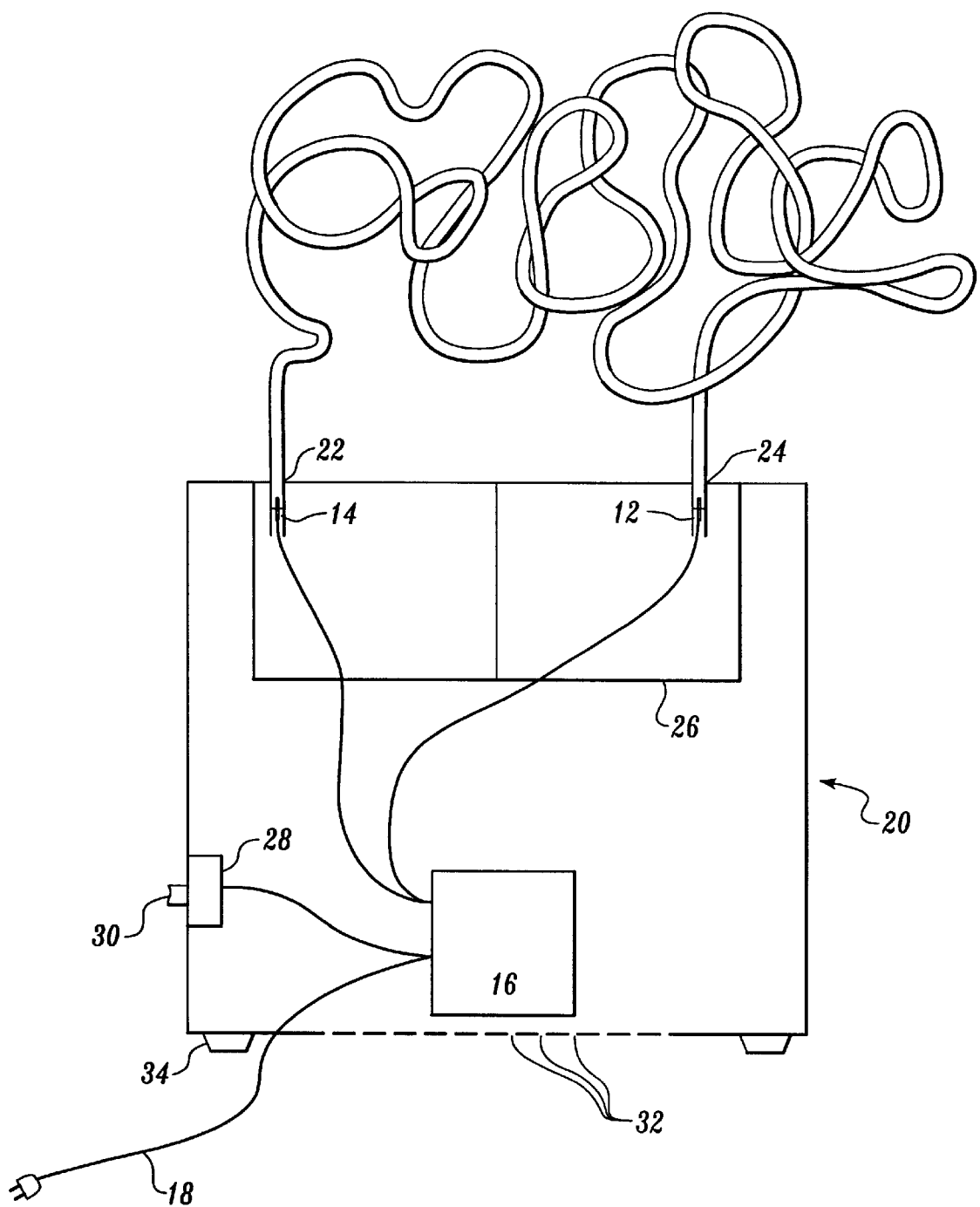
FIG. 2 schematically illustrates a three dimensional neon fixture, with the base partially broken away to illustrate the electrical components.

FIG. 2 illustrates a preferred embodiment of the neon fixture of the present invention wherein glass tubing 10 has a three dimensional convoluted configuration and is mounted in a housing for home, office or health care professional use. Tubing 10 has multiple bends and twists. The three dimensional arrangement provides a high level of illumination or color saturation in a relatively small volumetric area. Fixtures for use in treating light deficiency or mood disorders preferably comprises at least about 12 feet of glass tubing in a volumetric space of about 1.5 cubic feet. The length and diameter of the tubing may be adjusted to provide the desired illumination output, with longer lengths and smaller diameter tubing producing the highest illumination output. Multiple colors may be provided in a single fixture when the tubing is constructed by fusing multiple lengths of glass tubing. Tubing 10A, illustrated in FIG. 2, represents tubing having a different phosphor coating to produce a different color output. The three dimensional array, in addition to providing a compact fixture, substantially eliminates glare and the consequent side effects.

As shown in FIG. 2, tubing 10 terminates in electrodes 12, 14, which are electrically connected to transformer 16, connectable to an external electrical source via power cord 18. The electrical components are housed in base unit 20 having passages 22, 24 for receiving the terminal ends and electrodes 12, 14 of tubing 10. Electrodes 12, 14 are preferably mounted to a non-conductive, rigid mounting plate 26. Electrodes 12, 14 may be affixed to mounting plate 26, for example, by wire loops or other fastening means to stabilize tubing 10. A cushioning device, such as silicone, rubber, cork, or the like, is preferably provided between the electrodes and the mounting plate to prevent shifting of tubing 10 and to serve as a shock absorber if shifting does occur. Base 10 may have any desired configuration, so long as it provides a stable support for tubing 10.

The fixture illustrated in FIG. 2 also features a dimmer switch 28 electrically connected to transformer 16 and grounded power cord 18. Adjustable knob 30 permits a user to vary the illumination output of tubing 10, and thereby accommodate a variety of therapeutic needs. Perforations 32 are preferably provided in the floor or side of base unit 20 to ventilate and cool the electrical components. Ventilation through the floor of base 20 is enhanced by the use of mounts 34 that elevate the base unit from the surface on which it rests.

Figure 3:
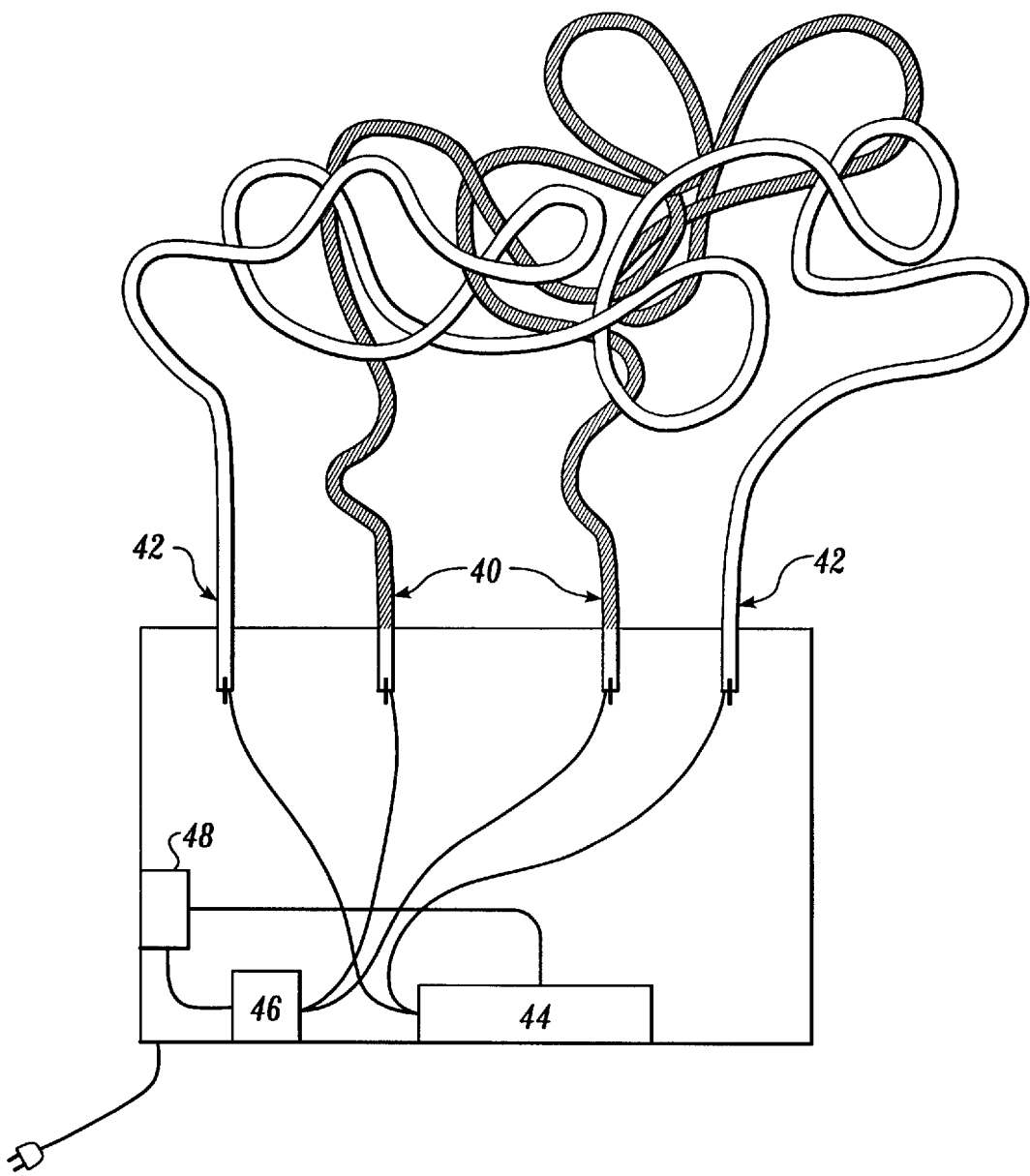
FIG. 3 schematically illustrates an illumination device including a timer that can simulate a natural light condition over time, such as sunrise, sunset, or the like, and is useful for treating patients having irregular sleep patterns.

FIG. 3 illustrates a specialized illumination device according to the present invention that uses a timer and multiple light sources to simulate changes in lighting conditions, such as sunrise. This fixture employs multiple illumination sources or glass tubing units 40 and 42, which preferably provide neon light of different wavelengths. Each illumination source is similar to the source illustrated in FIG. 2 and each is electrically connected a transformer. In the illustrated embodiment, illumination source 40 is connected to transformer 44, while illumination source 42 is connected to a second transformer 46. One or both of the transformers, is capable of ramping up to full voltage output over a specified time period, and, thus produce increases or decreases in illumination over time. One or both of the transformers is electrically connected to a timer 48.

An especially preferred embodiment of the device illustrated in FIG. 3 can be constructed to simulate a natural sunrise or sunset, or other light changing circumstance. In this embodiment, illumination source 42 emits rose-colored light and illumination source 40 emits white light. Illumination source 40 simulates daylight, and an appropriate length and diameter of tubing having a white phosphor coating is selected depending upon the illumination level desired. Illumination source 42 simulates dawn, and a considerably lower level of illumination is generally required of this source. Timer 48 activates transformer 46, and thereby illumination source 42 at fall illumination to simulate dawn. When illumination source 42 is activated, the timer activates transformer 44, which ramps up the voltage supplied to illumination source 40 such that it reaches full illumination over a pre-determined or manually selectable period of time, e.g. 1.5 hours. Thus, the white light reaches full illumination over the course of time. It will be obvious to one of ordinary skill in the art that devices may be constructed to simulate other natural or artificial light conditions.

Figure 4:
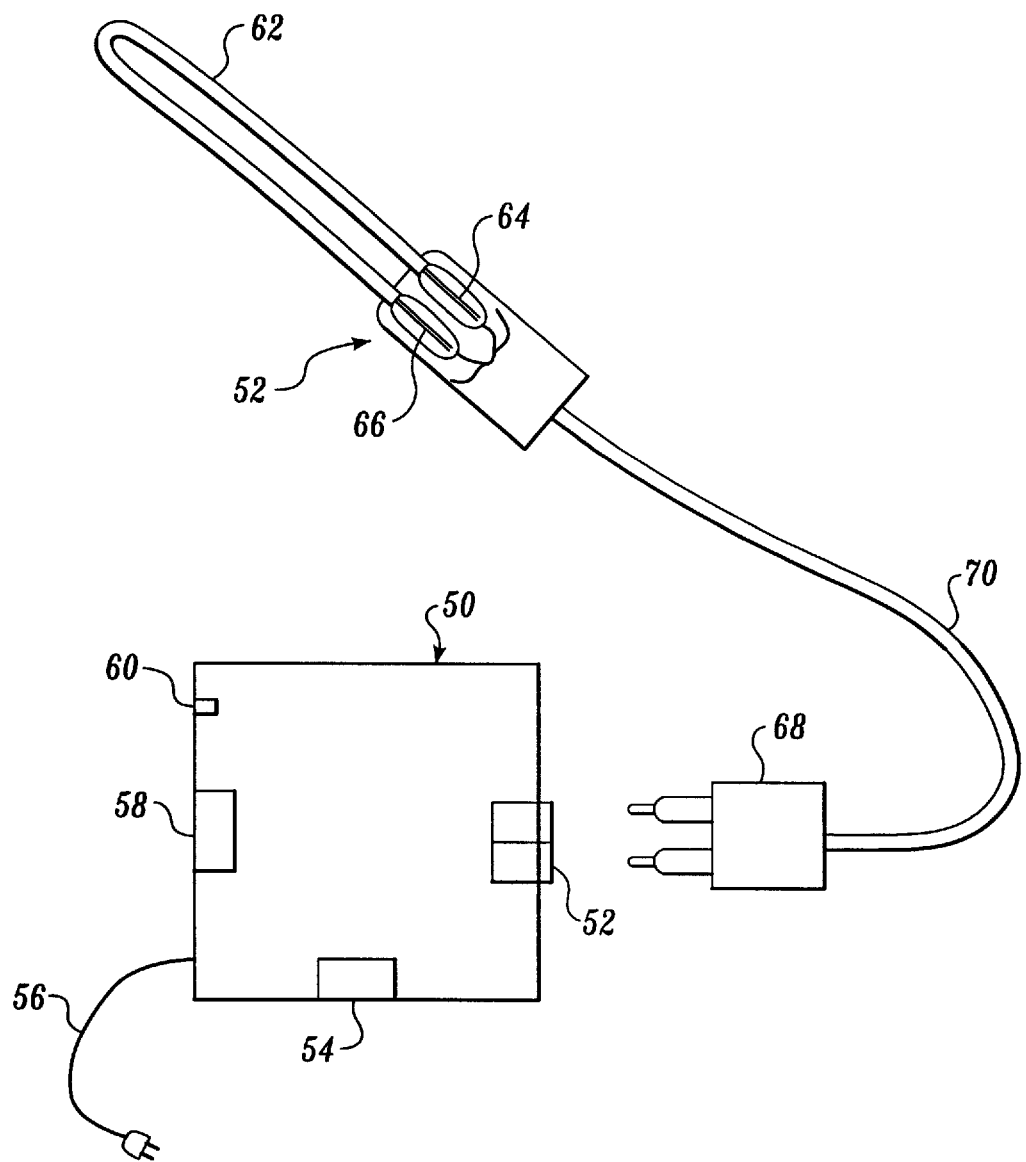
FIG. 4 schematically illustrates an illumination device including a removable wand-type structure that is especially suitable for color therapy treatments.

FIG. 4 illustrates yet another embodiment of the present invention in which the illumination source is provided as a structure which can be moved and manipulated to provide light in close proximity to an area to be treated. Fixtures of this type are preferably provided with interchangeable illumination sources such that a base or power unit 50 may be used with a variety of illumination sources 52 having different illumination, color and color saturation outputs useful for a variety of treatments. This embodiment is especially suitable for use in connection with color therapy and may advantageously provide an illumination source emitting light of selected wavelengths that can be used in proximity to or applied to acupressure or acupuncture points or to other anatomical locations for focused treatment.

The fixture of FIG. 4 comprises a base or power unit 50 having a high voltage socket 52 electrically connected to a transformer 54, which is electrically connected to a grounded power cord 56 and activation switch 58. Indicator light 60 is preferably provided to provide a visible indication when the fixture is activated. Illumination source 52 comprises a length of glass tubing 62 enclosing an illumination gas. The ends and electrodes 64, 66 of glass tubing 62 terminate in a handle structure, with electrodes 64, 66 being electrically connected to high voltage plug 68 via cord 70. The glass tubing is thus mounted in a hand-held unit that is electrically connected to but movable independently of power unit 50. The illumination source may be provided as a generally two or three dimensional structure, as described previously. Glass tubing having white or colored phosphor coating(s) may be employed, depending on the application.

Figure 5:
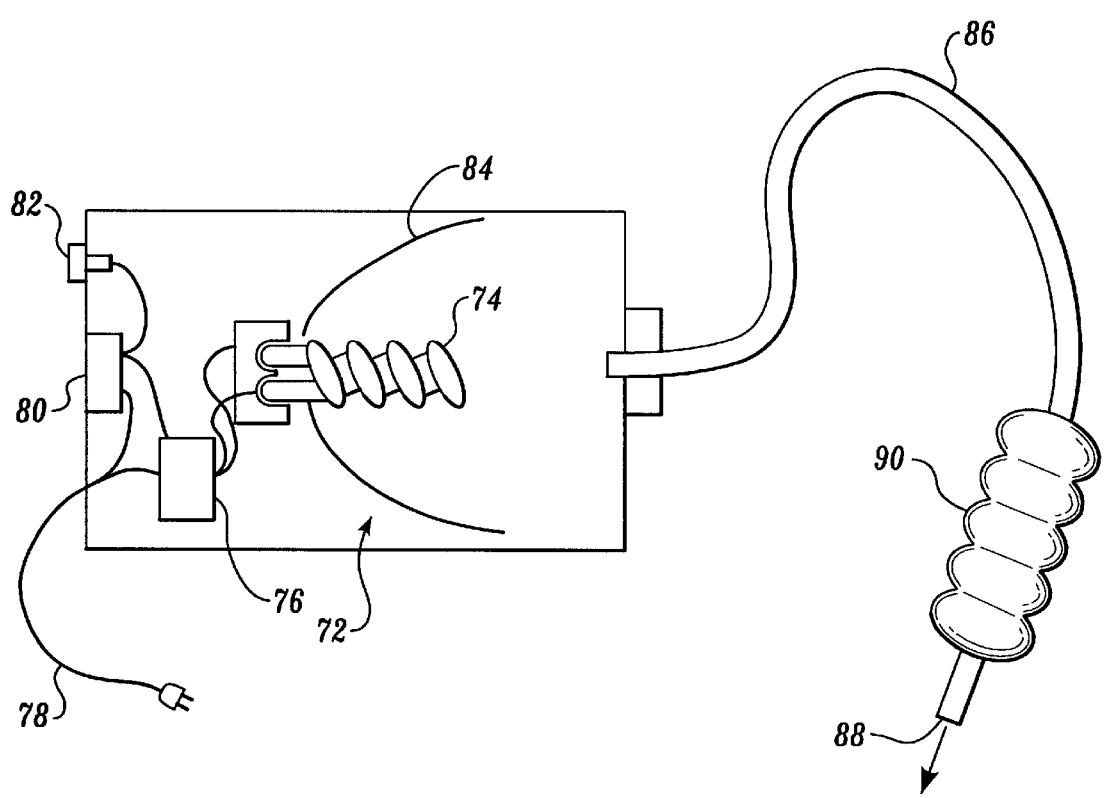
FIG. 5 schematically illustrates a combination neon and fiber optic cable illumination device.

FIG. 5 illustrates yet another embodiment of the present invention in which a neon illumination source serves as a source for transmitting light through fiber optic cables to provide a focused light source. In FIG. 5, base unit 72 comprises a neon illumination source 74 electrically connected to a transformer 76, which is electrically connected to a grounded power cord 78 and an activation switch 80. Indicator light 82 is preferably provided to provide a visible indication when the fixture is activated. Illumination source 74 comprises a length of glass tubing enclosing an illumination gas and may be provided as a generally two or three dimensional structure. Illumination source 74 is preferably removable from a mounting socket installed in base unit 72 so that illumination sources having different illumination outputs, configurations and colors can be used interchangeably in the fixture. A reflective surface 84, such as a parabolic reflector, may be provided to direct the output of illumination source 74 toward the source end of fiber optic bundle 86. Light from illumination source 74 is thus transmitted along fiber optic cable bundle 86 to light output 88, which provides a relatively focused light output that can be applied to acupressure and acupuncture points, or other locations, for light and/or color therapy treatments. A handle or grip 90 may be provided in proximity to light output 88 for convenience during treatment.

Numerous embodiments utilizing neon illumination sources and making use of fiber optic cables may be envisaged. This type of fixture is especially suitable for use in color therapy treatments.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

I claim:

1. A method for treating light deficiency and mood disorders, including exposing a patient to a fixture comprising a length of glass tubing terminating in an electrode at each end and enclosing an illumination gas comprising mercury vapor and at least about 50% neon, the electrodes being electrically connectable to a transformer, and the transformer being electrically connectable to a power source, the fixture having an illumination output of at least 2,500 lux at a distance of 18 inches.

2. A method as described in claim 1, wherein the fixture comprises glass tubing having a phosphor coating that produces broad spectrum white light.

3. A method as described in claim 2, wherein the fixture comprises a three dimensional arrangement of bent and convoluted glass tubing.

4. A method according to claim 1, wherein the glass tubing has a diameter of from about 7 mm to about 18 mm.

5. A method according to claim 1, wherein the glass tubing is provided in a three dimensional convoluted arrangement.

6. A method according to claim 5, wherein the tubing axis is continuously variable and scatters light randomly.

7. A method according to claim 1, wherein the fixture comprises at least about 12 feet of glass tubing in a volumetric space of about 1.5 cubic feet.

8. A method for treating light deficiency and mood disorders, including exposing a patient to a light fixture confining an illumination gas comprising at least about 50% neon gas with mercury vapor, the illumination gas capable of illuminating when activated by an electric current.

9. A method according to claim 8 for treating a light deficiency or mood disorder selected from the group consisting of: depression, seasonal affective disorder, stress, learning disabilities, pre-menstrual syndrome, sexual dysfunctions, visual disorders, immune and nervous system disorders and sleep and other natural rhythm disorders.

10. A method according to claim 8, wherein the illumination gas comprises at least about 80% neon gas.

11. A method according to claim 8, wherein the light fixture produces broad spectrum white light.

12. A method according to claim 8, wherein the light fixture produces light in one or more selected wavelength bands.

13. A method according to claim 8, wherein the light fixture comprises a three-dimensional arrangement of bent and convoluted glass tubing confining the neon-containing illumination gas.

\* \* \* \* \*